(12) United States Patent
Butner

(10) Patent No.: US 10,382,081 B2
(45) Date of Patent: Aug. 13, 2019

(54) RECORDAL OF POTENTIAL HARMFUL RADIATION

(71) Applicant: TRUST TECHNOLOGY WORLD DMCC, Dubai (AE)

(72) Inventor: Wayne Butner, Vancouver (CA)

(73) Assignee: TRUST TECHNOLOGY WORLD DMCC, Dubai (AE)

( * ) Notice: Subject to any disclaimer, the term of this patent is extended or adjusted under 35 U.S.C. 154(b) by 0 days.

(21) Appl. No.: 15/119,440

(22) PCT Filed: Feb. 20, 2015

(86) PCT No.: PCT/EP2015/053651
§ 371 (c)(1),
(2) Date: Aug. 17, 2016

(87) PCT Pub. No.: WO2015/124744
PCT Pub. Date: Aug. 27, 2015

(65) Prior Publication Data
US 2017/0063417 A1  Mar. 2, 2017

(30) Foreign Application Priority Data
Feb. 21, 2014 (GB) .................................. 1403053.0

(51) Int. Cl.
| *H04B 1/3827* | (2015.01) |
| *A61N 1/16* | (2006.01) |
| *H04M 1/21* | (2006.01) |
| *H04W 24/08* | (2009.01) |

(52) U.S. Cl.
CPC ............ *H04B 1/3838* (2013.01); *A61N 1/16* (2013.01); *H04M 1/21* (2013.01); *H04W 24/08* (2013.01)

(58) Field of Classification Search
CPC ....... H04B 1/3838; A61N 1/16; H04W 24/08; H04M 1/21
USPC ....................................................... 455/67.11
See application file for complete search history.

(56) References Cited

U.S. PATENT DOCUMENTS

| 5,544,665 A | 8/1996 | Litovitz et al. |
| 5,566,685 A | 10/1996 | Litovitz et al. |
| 8,401,488 B2 * | 3/2013 | Sulkowski, Jr. ... G01R 29/0814 342/445 |
| 2002/0011828 A1 | 1/2002 | Wallach |

(Continued)

FOREIGN PATENT DOCUMENTS

| CN | 201414156 | 2/2010 |
| GB | 2482421 | 2/2012 |

(Continued)

OTHER PUBLICATIONS

International Preliminary Report on Patentability for Application No. PCT/EP2015/053651 dated Sep. 1, 2016.

(Continued)

*Primary Examiner* — Eugene Yun
(74) *Attorney, Agent, or Firm* — The Dobrusin Law Firm, P.C; Daniela M. Thompson-Walters

(57) ABSTRACT

A personal communication device provided with means for the detection of potential harmful radiation emitted by the device and which is provided with a data memory module that records the characteristics of the data detected to provide real time data for the study of potentially harmful radiation.

21 Claims, 5 Drawing Sheets

(56) References Cited

U.S. PATENT DOCUMENTS

Figure 1:
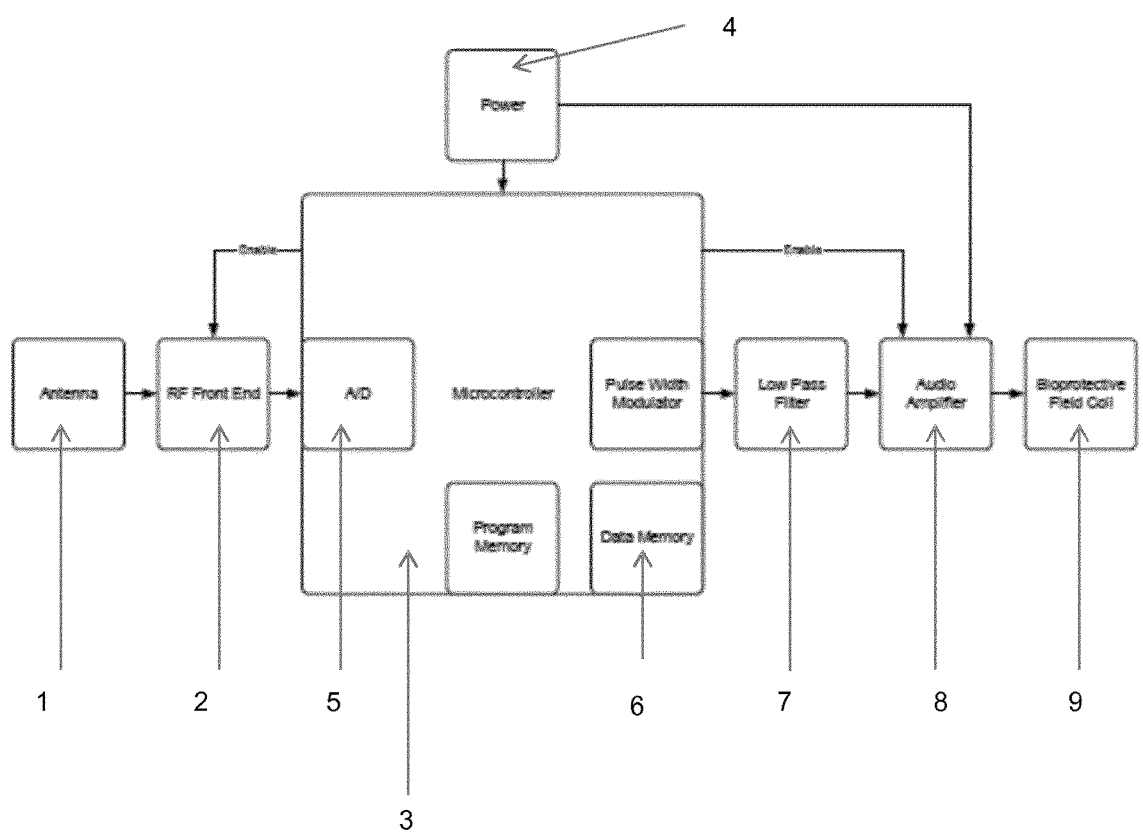

| | | |
|---|---|---|
| 2002/0016155 A1 | 2/2002 | Charbonnier |
| 2006/0008919 A1* | 1/2006 | Boay .................... G01N 21/783 |
| | | 436/164 |
| 2010/0056210 A1 | 3/2010 | Bychkov |
| 2010/0125438 A1 | 5/2010 | Audet |
| 2010/0203862 A1 | 8/2010 | Friedlander et al. |
| 2013/0203363 A1 | 8/2013 | Gratt et al. |
| 2013/0303092 A1 | 11/2013 | Penafiel |
| 2015/0162897 A1* | 6/2015 | Zachara ................. H01Q 21/28 |
| | | 455/77 |

FOREIGN PATENT DOCUMENTS

| | | |
|---|---|---|
| GB | 2484167 | 4/2012 |
| GB | 2484168 | 4/2012 |
| WO | 02/00468 | 1/2002 |

OTHER PUBLICATIONS

PCT Search Report dated Apr. 30, 2015 for Application No. PCT/EP2015/053651.
UK Search Report dated Jul. 24, 2014 for Application No. GB1403053.0.

* cited by examiner

RECORDAL OF POTENTIAL HARMFUL RADIATION

The present invention relates to the detection and recordal of potentially harmful electric fields, magnetic fields and electromagnetic fields. In particular radiation from modern day battery powered mobile telecommunications devices which are used for a variety of functions including both voice and data transmission. Information that may be recorded includes one or more of the communication mode, the protocol of the device, the signal strength and power level and the signal duration. The invention can additionally relate to systems that provides a remedial signal for the potentially harmful radiation and also provides for the recordal of the characteristics of the remedial signal.

All electromagnetic radiation consists of oscillating electric and magnetic fields and the frequency, which is the number of times per second at which the wave oscillates, determines their properties and the use that can be made of them. Frequencies are measured in hertz or Hz, where 1 Hz is one oscillation per second, 1 kHz a thousand, 1 MHz is a million, and GHz, is a thousand million. Frequencies between 30 KHz and 300 GHz are widely used for telecommunications, including broadcast radio and television, and comprise the radio frequency band.

Cellular mobile services operate at frequencies authorised by governments and typically operate within the frequency ranges 872-960 MHz, 1710-1875 MHz and 1920-2170 MHz. These frequencies are within the microwave frequency band which encompasses the range between 300 MHz and 300 GHz. Other applications within this range include radar, telecommunication links, satellite communications, weather observation and medical diathermy. This invention is particularly useful with devices that operate on frequencies used for cellular telephones.

A radio frequency wave used to carry information in radio communications is referred to as a carrier wave. The radio frequency carrier wave of any system is produced by the transmitter as a sine wave, or other regular waveform. A carrier wave conveys no information if its properties do not vary in time. If the carrier wave is to convey any information, for instance, speech, music or digitized data, this information has to be added to it in some way. The process of varying one or more properties of a carrier signal with respect to the information that it is to carry is known as modulation. Properties of the carrier wave that may be varied through modulation include for instance, amplitude, frequency, phase or any combination of these. For example, for AM (amplitude modulation) transmission, the electrical signal from a microphone produced by speech or music is used to vary the amplitude of the carrier wave, so that at any instant the size or amplitude of the RF carrier wave is made proportional to the size of the electrical modulating signal. In FM (frequency modulation), the instantaneous frequency of the carrier deviates from the carrier frequency by an amount dependent on the strength of the modulating signal. Phase modulation (PM) is a form of modulation that represents information as variations in the instantaneous phase of a carrier wave. FM and PM are very commonly used for current day radio communications.

A mobile phone (cell phone) sends and receives information (voice messages, text messages, emails, fax, computer data, downloads information etc) by radio communication. Radio frequency signals are transmitted from the phone to the nearest base station and incoming signals (carrying the information from the source to which the phone user is listening) are sent from the base station to the phone at a slightly different frequency. Base stations link mobile phones to the rest of the mobile and fixed phone network. Once the signal reaches a base station it can be transmitted to the main telephone network, usually by an optical fiber network.

Each base station provides radio coverage to a geographical area known as a cell. Base stations (BS) are connected to one another by a mobile services switching centre (MSC), which tracks calls and transfer them as the caller moves from one cell to the next. An ideal network may be envisaged as consisting of a mesh of hexagonal cells, each with a base station at its centre. The cells overlap at the edges to ensure the mobile phone users always remain within range of the base station. Without sufficient base stations in the right locations, mobile phones will not work. If a person with a mobile phone starts to move out of one cell into another, the controlling network hands over communications to the adjacent base station.

The potentially harmful radiation with which this invention is particularly concerned is that emitted by the cellular telephone when it is transmitting or receiving information especially voice information and particularly when it is transmitting voice information as this tends to generate more RF signals and in particular when it is transmitting or receiving speech as that is generally the time when it is in closest proximity to the head, and transmission radiation occurs for a significant length of time.

There are conflicting views as to the effects of electric fields, magnetic fields and electromagnetic fields on living systems. However there is considerable evidence that certain fields may be damaging to living systems including humans. It may also be that the detrimental effects are long term and their full impact has not yet been realised. There is however a lack of reliable, real time data and evidence to draw any firm conclusions on the subject.

There has been a dramatic increase around the world in the use of electrically operated devices particularly battery powered hand held mobile telephones. All such devices have associated with them electromagnetic field emissions which, to varying degrees, have the potential to affect human health. Of particular interest are devices that transmit radio frequency (RF) signals and are used in close proximity to the human body particularly the head, for instance cellular phones and other personal communication devices. At issue is the possibility that the safety standards under which these devices are manufactured which establish RF exposure limits to the users of these devices may not adequately account for effects below the thermal threshold, that is, at exposure levels well below levels that can produce measureable heating and can be attributed to direct energy transfer. The potential for such low level effects is supported by substantial evidence from epidemiologic studies and laboratory research which suggests that any measures that could reduce and/or minimize the effects of such exposure would be beneficial to the users of these devices.

U.S. Pat. No. 5,544,665 is concerned with the protection of living systems from the harmful effects of electromagnetic fields and states that certain fields have an effect on the enzyme omithine decarboxylase. The patent states that the potentially damaging effect can be reduced or eliminated if the detrimental electromagnetic field is altered either by switching the field on and off or superimposing an electromagnetic noise field upon it. The patent further states that the effect can only be reduced if such alteration causes relevant characteristic properties of the field to change in time at intervals of less than 5 seconds and preferably at intervals from 0.1 to 1 second. The characteristic properties that can be changed are said to be frequency, phase, direction, waveform or amplitude. Similar effects are discussed in Bioelectromagnetics 14 395-403 (1993) and Bioelectromagnetics 18 388-395 (1997). U.S. Pat. No. 5,544,665 further describes various applications of the bio-protection scheme including applications to cellular telephones of the type available in the late 1980's which were bulky and used only for voice transmission.

The noise was generated by a coil forming part of the battery pack. Activation of the noise was accomplished by monitoring the flow of electric current from the battery to the phone and using this as an indirect means to determine when the phone was transmitting RF fields that were likely to produce biological effects. This activation technique worked reasonably well with older phones but proved to be unreliable with newer phones which have applications, such as data transmissions, games and other entertainment applications that demand power from the battery, thereby causing the flow of electric current, that could cause false triggering of the noise and potentially unnecessary and unacceptable reduction in battery life.

In WO 2012/041514 we describe a device provided with means to reduce or eliminate the potentially harmful effect of the RF signals and further provided with a means to sense and analyse RF fields and determine their ability to produce biological effects, and which activates the means to reduce or eliminate the potentially harmful effect of the measured RF signals on humans or animal life.

In GB Patent Applications 1403056.3 and 1423184.9 we provide a remedial device for the reduction or elimination of the potentially harmful effect on humans or animal life caused by exposure to electromagnetic fields produced by devices that are battery operated to transmit RF signals containing a module for the detection and analysis of the communication protocol, the mode of communication and the strength or power of the signal in operation that generates the RF signals wherein said module is powered by the battery of the device. When the presence of potentially harmful radiation is detected the detection activates a remedial signal generator.

There is however a need to collect and analyse data relating to both the emitted potentially harmful radiation and the remedial signal. According to the present invention the detector module of such a system includes a data memory facility which records signal parameters relevant to the determination of biological impact of the detected signal on the basis that the determination can be made from measurements of the low frequency envelope, including the amplitude of the signal over a minimum sampling interval. In a further embodiment the data memory facility also records the parameters of any remedial signal that may be generated.

The memory facility may be employed without the generation of a remedial signal and it may be used solely for accumulating data concerning the generation of potentially harmful radiation such as information selected from the communication mode and protocol of the device, the strength and power level and duration of the signal. Alternatively and in a preferred embodiment the data memory facility is employed in a device that also generates a remedial signal for the detected potentially harmful radiation. In this instance as a desirable option the memory facility can also record the characteristics of the remedial signal generated by the device and as with the recordal of the potentially damaging radiation it can record the power and the strength, the frequency and the elapsed time for which the remedial radiation is generated. In one embodiment the remedial signal can be generated according to the recording of the detected signal.

The data memory facility may simply store the recorded information for subsequent download perhaps by removing the data memory and downloading the information stored therein. Alternatively the recorded information can be downloaded by placing a receiver equipped with means of transmission which may be wired or wireless in order to download the recorded data for analysis. In a preferred embodiment however the data memory facility may be provided with a transmitter which enables the data recorded to be transmitted, as required, to a remote location for subsequent analysis, typically through the mobile telephone network.

In its broadest embodiment the invention therefore provides a personal communication device such as a battery powered telecommunication handset provided with means for the detection of potential harmful radiation emitted by the handset wherein the device is further provided with a data memory facility that records characteristics of the data detected by the means for detection, in particular the data memory facility records one or more of the following information, the communication mode and protocol of the device, the strength and/or power level of the radiation emitted by the device and the duration of the generation of the radiation.

In a second embodiment the personal communication device further contains means for transmission of the data recorded concerning the potentially harmful radiation to a remote location, preferably over the mobile telephone communication network.

In a third embodiment the personal communication device further contains means for generating a remedial radiation to reduce the potential harm of the potential harmful radiation that is detected and in a further embodiment the memory facility records one or more of the strength and/or power and the duration of the generation of the remedial signal.

In a further embodiment the personal communication device further contains a means for the recordal of characteristics of the remedial signal that is generated. Preferably the same data recording facility is employed for recording characteristics of both the potentially harmful radiation and the remedial radiation. This could be useful in situations where one wishes to verify the activation of the remedial signal. When the personal communication device is a portable telephone the memory facility may be provided in the handset of the device or in the case or in the battery system.

In one embodiment the operation of the handset of the personal communication device can activate the recordal facility and, if required, the remedial signal generator. For example the recorded facility can be activated by sensing if one or more of the transceivers of the personal communication device are in operation.

Any characteristic of radiation such as amplitude, frequency and duration of the signal(s) may be recorded.

It is further preferred that a transmitter be provided within the personal communication device so that it can also transmit the data recorded concerning the potentially harmful radiation and the remedial radiation. Conveniently the same transmitter may be used to transmit the data recorded concerning the characteristics of both the potentially harmful radiation and the remedial radiation. This could be useful in situations where one wishes to verify the activation of the remedial signal.

The detection mechanism can be contained in the battery, the case or the handset itself.

The detection mechanism can be
a) powered by the handset battery if it resides within the handset battery,
b) powered by the handset battery if it operates within the handset microprocessor, program memory and data memory,
c) powered by the handset battery if it operates within a case that does not contain a battery, or
d) powered by the case battery if it operates within the case which contains a battery.

In a preferred system such as that described in GB Patent Applications 1403056.3 and 1423184.9 the detector module measures the amplitude and the timing of the low frequency envelope of the detected RF radiation. The signals may then be analysed to differentiate the communication modes that are related to voice communication (where the handset would be close to the users head) and other wireless signals such as data communication. By way of example the analysis can differentiate between GSM, 3G or 4G protocols and between voice and data communication modes for 3G or 4G systems. The differentiation is preferably performed by an analysis module within a microcontroller that is programmed to detect the different communication protocols and modes. Once detected and analysed the data recordal facility can be activated by the microcontroller by powering the battery of the mobile telecommunication device to record the characteristics of the potentially damaging signal. The memory facility can be configured to record such differentiated radiation. Alternatively the recorded data may be communicated to the personal communication device via a communication interface such as near field communication or blue tooth.

If a remedial signal generator is also present it can be switched on if the detected signal is deemed to be potentially damaging and the strength of the remedial signal can be tailored to the nature of the radiation that has been sensed. For example, if the remedial signal strength in relation to GSM communication is deemed to be 100%, for voice communication for 3G, 50% may be sufficient whereas for 3G data communication 25% may be required. The micro controller can be programmed to cause the remedial signal generator to provide signals of the appropriate strength according to the analysis of the signals received. If required the data recordal facility is simultaneously activated in order to record the characteristics of the remedial signal that is provided.

The detector is preferably an antenna.

As described in GB Applications 1403056.3 and 1423184.9 entitled Remedial Signal Generation, in a preferred embodiment power management is provided using a timer that switches on and off the power supply to a component of the detection module and the recordal module as well as to the remedial signal module when used to minimise the power drain from the battery and yet provide active (powered) detection and recordal of the potentially harmful signals. The timer should be one that requires a minimal power for operation and is directly connected to the battery. The timer preferably has a wake up interval to preserve battery strength and the wake up interval should be sufficiently small to allow analysis of any Radio Frequency signals detected by the antenna so as to determine if there are any harmful signals in time to activate recordal module and the remedial signal generator if used.

Use of such a system minimizes power consumption while still allowing monitoring and recordal of the RF field when needed. In the preferred embodiment means are provided to monitor the power drain and the application conditions are monitored and the power drain is set accordingly. The power management control may conveniently be implemented by software which is executed within a microcontroller which switches the recordal and optional transmitter on and off. Many other functions can be implemented within such a microcontroller.

The invention may be applied to record information from most electronic devices that operate by transmitting RF signals which could be potentially harmful to human or animal life, but it is particularly useful with battery powered personal communication devices, such as cellular telephones, that are used in close proximity to the human body particularly to the head. In a preferred embodiment the invention provides a system that can be readily adapted for use with a variety of mobile phone designs and their associated batteries.

Earlier studies have shown that RF radiation can cause potentially harmful effects if it is regular, meaning that it has constant properties, and is continuously applied for periods of over 10 seconds and that the potential harm can be substantially eliminated if the regularity period is reduced to no more than 1 second. Studies further exploring these results will be useful and the present invention will provide more reliable and accurate real time data to improve such studies. The means to eliminate the potential harm may superimpose a noise electromagnetic field on the potentially harmful radiation to produce a combined field that is irregular in time, meaning that it does not have constant properties in time, and therefore no longer has the potential to cause harm. Use of the noise field, which is herein referred to as the remedial signal, is preferred as it allows for use of the electronic device without altering the manner in which it operates.

The invention is particularly useful for obtaining information concerning the operation of battery operated personal communication devices. In the preferred embodiment the potentially harmful effect of the RF radiation is inhibited by a means that generates an appropriate remedial signal that is superimposed on the RF signal to provide a combined signal that is irregular and therefore has no bio-effecting consequence and the invention allows one to obtain detailed, accurate, real time and reliable information concerning such activities. Any suitable means may be used to produce the remedial signal and the means may comprise an inductive coil which is activated to produce the remedial signal field, primarily magnetic in nature, employing power from the battery of the cellular telephone.

The means which senses and identifies the potentially harmful radiation may be any standard RF sensor. We prefer to use an antenna, with accompanying electronics, which have been suitably configured to identify the particular radiation which is emitted by the electronic device and which is considered to be potentially harmful.

The antenna is preferably a wire such as a copper wire which can be fitted into any convenient space within an existing telephone handset without requiring any significant modification thereof. Additionally the means may be provided with means to differentiate the nature of the radiation according to the communication mode that is being employed. In order to enhance the sensitivity of the device it is preferred to amplify the signal received prior to analysis and accordingly the sensing means such includes an amplifier in addition to the preferred antenna. The detection means will be coupled to the recordal means so that the data as analysed is passed to the recordal means and recorded. Alternatively the operation of devices such as transceivers within the handset can be used to indicate that potentially harmful radiation is likely being generated and the recordal facility activated accordingly.

The system of the invention may be formed to fit within existing cellular phone handsets or other personal communication devices, with little or no modification to the devices. For instance, the recordal facility may be provided in a component which may be incorporated inside the handset and maybe in association with the battery pack that provides power to the handset. The preferred system comprises an electronic circuit that comprises in addition to the memory facility and any transmitter that may be used an RF antenna, a microcontroller that operates various modules, an analysis module and optionally a remedial signal activation module and a coil for generating the remedial signal field. When present the coil may be formed around the battery of the handset. Where the battery is lithium polymer, the coil may be physically pressed into the battery, so as to minimize the space needed to fit this part. Alternatively the system may be separate from the battery within the handset, or separate from the handset but adapted to be placed next to the handset while the handset is in use to provide a remedial signal. For example recordal facility may be provided with a component formed as a card article, of credit card dimensions and shape, with electronics incorporated within the card, and a coil for providing the remedial signal being formed around the edge of the card.

The system is preferably managed by a microcontroller which is programmed to control the operation of the various modules including reaction to the analysis of the received signal and operation of the memory facility within the personal communication device and any transmitter therein and it can further activate an appropriate remedial signal. In a preferred embodiment the microcontroller overseas the operation of the system and additionally can sense the remaining capacity of the battery and transition the system to storage mode minimizing current consumption prior to recharging. When the operation of the handset is used to activate the recordal facility this may be accomplished by programming the microprocessor of the handset.

The invention therefore provides more specifically, means for monitoring the activities of a remedial device for association with a battery powered personal communication device that emits RF transmissions potentially harmful to humans or animal life, the remedial device including sensor means for sensing the presence of said RF transmissions, signal analysis means for assessing the RF transmissions to determine if they are likely to cause biological effects, and a remedial signal generator means also operated by the battery, said signal analysis means being coupled for activation of a memory facility and when present actuation of said remedial signal generator means. The remedial signal generation means being arranged to establish a remedial electromagnetic field in the vicinity of the handset. In a preferred embodiment the sensor means is linked to the battery and is preferably linked by an on/off timer to conserve power drain from the battery. In the preferred embodiment the signal analysis means differentiates between signals generated by voice communication and those generated by other forms of communication such as data communication so as to activate the appropriate remedial signal.

When an RF sensor is employed it is preferably an antenna, which has been suitably configured to detect the particular radiation which is emitted by the electronic device and which is considered to be potentially harmful. The antenna may be positioned anywhere within the telephone handset and should be responsive to a carrier wave frequency of the cellular handset that is a microwave frequency in the region of 0.8 to 2 GHz, as detailed below. (As an alternative to a separate antenna, the coil for establishing the remedial field may be configured to detect RF transmissions.)

The RF detection stage, for detecting RF transmissions that may contain potentially harmful components, preferably includes a signal analysis means, which signal analysis means is arranged to make an analysis of the detected RF transmissions in order to make a determination of whether components present in the transmission signal are potentially harmful components and also the nature of signals within the potentially harmful components to determine the communication responsible and activate the remedial signal accordingly. The RF detection stage may be arranged to provide an actuation signal to the signal analysis means. The detection stage may be activated by the battery of the handset perhaps through use of a timer and is arranged to monitor RF emissions from the handset, and to rectify and integrate an RF transmission signal. The amplitude and timing of the detected signal are determined and compared with the current version, in order to determine whether there is RF radiation of significant duration that is likely to cause biological effects. This is typically the case during speech transmission to and from the handset.

Although the detected signal may be of low strength it may still be potentially damaging to health and we prefer to provide an amplifier between the active detector and the analysis module to enable detailed analysis and good use of the signal.

The preferred use of an active detection module therefore allows for amplification and more accurate evaluation of the antenna signal. The active detection of the antenna signal on successive time intervals generates a signal that can be analysed typically by software within the microcontroller to indicate the type of signal detected. The signal detection interval of the active stage should be preferably between 100 ms and 1 s. The output of the active detector may then be employed to activate a remedial signal generator via a remedial signal control module. The signal analysis means can make an accurate and reliable determination of the characteristics of the sensed RF signal, in particular, whether the transmission is voice or data and the likely transmission protocol, for instance, GSM, 3G or other commonly used protocols, and whether the particular type of transmission contains potentially harmful components of any nature. The information created by such an analysis may then be recorded in the recordal facility.

The signal analysis means may provide an activation signal to a power control module within the microcontroller to enable supply of power to the data recordal facility and any associated transmitter as well as any remedial signal generator that is employed (or selected parts thereof). The remedial control generator may include a remedial signal control module, which provides a control signal to the power source, and a control signal to a remedial signal generator module, for generating the desired form of remedial signal. In the preferred embodiment the remedial signal control module is responsive to an output from the RF detection stage, and is preferably provided within a microcontroller for executing one or more algorithms for controlling the remedial signal generator module. As preferred, the control module waits for a period of about 1 second until it receives a continual output from the detection stages, and then requests the power unit to provide power to the generator module, so that the remedial signal is generated for a period of about 3 seconds. The waiting period of about 1 second is significant in that it represents a minimum period in which the presence of an RF signal may trigger a response in living tissue. Any radiation generated by the handset for a period of less than this minimum period is regarded as not requiring remedial action. The period of 3 seconds is chosen on the grounds of convenience, since with a longer period, a remedial field may be generated when it is not required, and a shorter period may result in excessive switching operations within the circuitry. At the end of the 3 second period, the control module is reset unless or until a continual signal is again present from the RF detection stages.

The remedial signal generator module may include a digital noise generator, which is coupled through digital to analog conversion means and filter means, for providing an analog form of the remedial signal, to a coil which provides a means for establishing the remedial field in the neighbourhood of the handset.

In operation therefore the cellular telephone will be activated for use and will immediately generate the potentially harmful radiation at the particular predetermined frequency. The presence of the radiation will immediately be sensed by either the detection means or the activation of components within the handset and analysed by the sensor and detection means, which will then activate the data recordal facility and any transmitter that may be used as well as the remedial signal (noise) generator means that converts the constant potentially harmful radiation to a random benign wave pattern if used. The detection means can also detect when the potentially harmful radiation is no longer being generated and deactivate the memory facility and the remedial signal if used until the next time that they are required. The choice of the remedial signal will depend upon the nature of the device and the type of the potentially harmful waves it generates. However we have found that for negating the potentially harmful effect of the radiation generated by use of a cellular telephone a remedial signal having a frequency in the range 30 Hz to 90 Hz and an amplitude indicated by the assessment of the detected RF signal.

An important aspect of a preferred embodiment of the invention is that the memory facility and transmitter as well as the radiation sensor and detector and the generator of the remedial signal can be incorporated into the cellular telephone without the need to alter the structure of the cellular telephone itself. When the System, including harmful signal detection, protection signal generation and recordal facility, is implemented in a mobile telephone directly (without involving the battery or case), the mobile telephones existing microprocessor, program memory and data memory can be utilized to implement the system. Additionally the mobile telephone handset will be modified to include the protection signal generator components including a coil and possibly a digital to analog converter and driver. An additional 'microcontroller' will not be utilized. The mobile telephone's microprocessor can then direct functions including memory facility. In order to be useful in mobile telephones the remedial device should preferably fit within conventional handsets without requiring modification of the handsets. It is therefore important that the various components are miniaturized. Additionally it is important that the device is flexible and readily adaptable so that it can be used in a wide variety of handsets. The preferred device therefore contains a microcontroller which incorporates and directs many of the functions of the device such as the memory facility and any transmitter and the RF signal analysers, the RF signal generator, the modulator and its VCA function, the integrator function, an ND converter may all be included within the microcontroller. Use of such a microcontroller together with a small antenna and a miniaturised remedial signal generator (such as a coil) provides a miniaturised system useful with a wide range of handsets and also with a wide range of batteries. As previously described when used the antenna may also be compact to fit within existing mobile telephone handsets. A copper wire is particularly useful.

The invention may be used with any of the battery cells used for cellular telephones such as lithium ion batteries but use with the softer batteries such as lithium polymer batteries may be advantageous since the printed circuit board containing the components of the system of this invention and the coil can be pressed into the battery casing to provide a battery with minimal reduction in battery capacity relative to a standard equivalent battery.

FIG. 1 hereto is a schematic illustration of the architecture of a data recordal system according to the present invention.

The system comprises a detector for Radio Frequency Signals such as the Antenna (1) which feeds information concerning the signals it detects into the Radio Frequency Front End detector (2) which is powered on instruction from the microcontroller (3) from a power source (4) which is typically the battery of the mobile telephone handset. The signal which may be amplified in the RF Front End then passes to an analogue/digital convertor (5) which may be within the microcontroller (3). The signal is then analysed to determine if it includes potentially harmful radiation and if so the nature of the radiation, the analysis being performed within the microcontroller (3). Based on the nature of the signal analyser the microcontroller passes a signal to activate a memory module (6) which records the characteristics of the signal. Optionally the microcontroller may also activate a transmitter (not shown). The microcontroller may also activate the remedial signal generator which is typically a bioprotective field coil (9). The signal preferably passes through a low pass filter (7) through an audio amplifier (8) which is powered by the power source (4) to the coil. The characteristics of this signal may also be recorded in the memory module so that the characteristics of both the potentially damaging radiation and of the bioprotective remedial field are recorded. The microcontroller may also be provided with means (not shown) for verifying the charge remaining in the power source and for moving the system to a storage mode when the charge is low and waiting for recharging.

Figure 2:
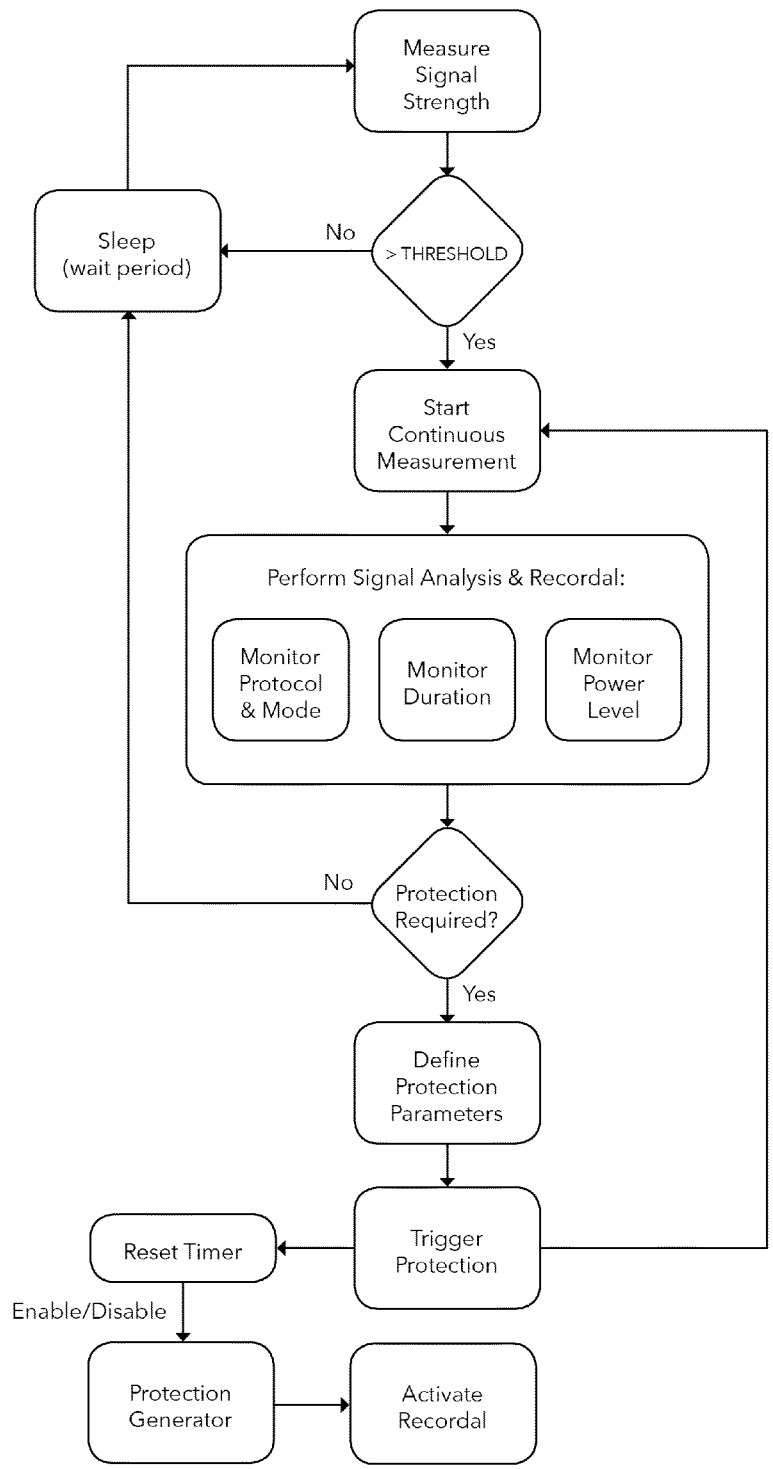

The operation of the embodiment shown in FIG. 1 is illustrated by the activity flow chart that is FIG. 2 hereof.

In the embodiment illustrated in FIG. 2 the device of the invention includes means for detecting the radio frequency (RF) signal emitted by a personal communication device. The detection means determines the power or strength of the signal and determines if it has the potential to be harmful and contains a memory module for recording data obtained from the determination. If the signal is weak and is deemed not to be potentially harmful the detection means is deactivated for a certain period of time after which it is reactivated to verify if the situation has changed.

If however the signal is considered to have a strength that is potentially harmful several continuous measurements of the signal may be taken and analysed to determine the protocol (GSM, 3G, 4G etc) and mode (voice or data) of the signal and also the power level of the signal and the duration of the signal which can all be recorded if desired. This determination indicates if a remedial signal is required. The results of this determination can be recorded in the memory module. If the determination is that no remedial signal is required as indicated by any one or any combination of the aspects analysed the device will be deactivated for a certain period of time after which it can be reactivated to verify if the situation has changed.

If however the determination is that a remedial signal is required then the device determines the nature and level of remedial signal required based on the analysis of the recorded signal (protocol, mode, power, duration etc) and then activates the generation of the appropriate remedial signal. In a preferred embodiment the remedial signal generator contains a timer which ensures that the remedial signal is provided for at least a certain period of time. The timer being such that the provision of the remedial signal can only be deactivated after a specified period of time after the overall detection system concludes that a remedial signal is no longer required. This ensures that the remedial signal continues to be provided for a certain period of time beyond the conclusion of the overall detection system so that the remedial signal is effective. The provision of the remedial signal, the power and for strength and the duration of the remedial signal may be recorded in the memory module.

The entire system as described can be contained within a microprocessor and may be activated by the initial determination of the radiation by an antenna. The microprocessor being provided as a component within the communication device or as part of the battery or case system.

The system provides useful real time data concerning the generation of potentially harmful radiation from portable communication devices.

Figure 3:
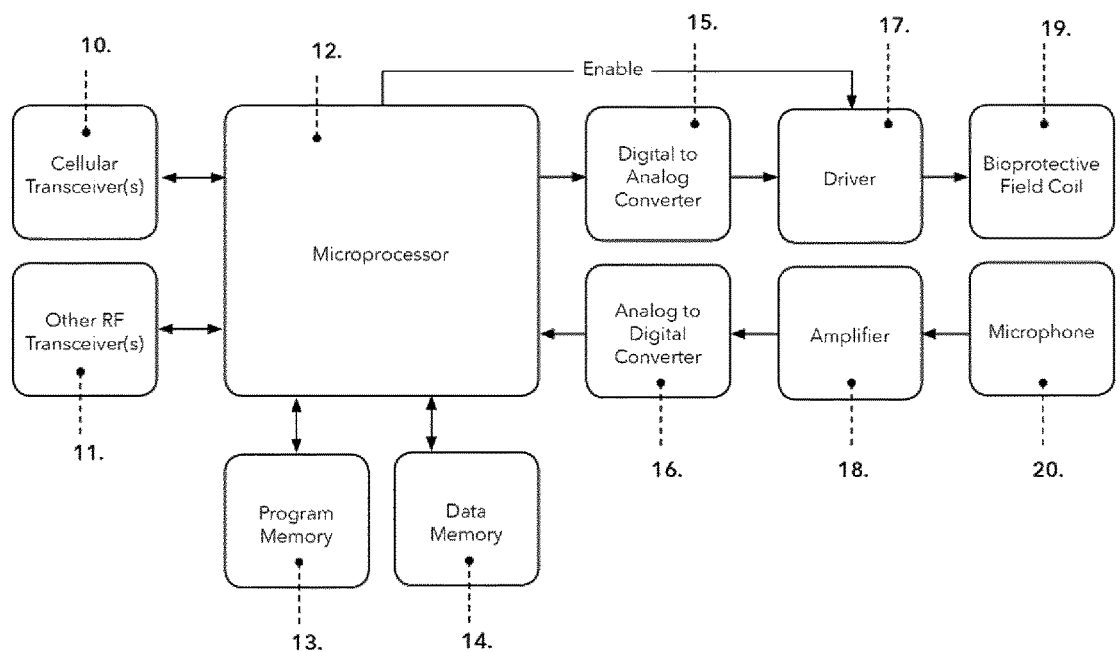

FIG. 3 shows an alternative architecture in which the operation of the cellular phone transceivers is used to activate the system. In this system when one or both of the transceivers (10 and 11) are active this is relayed to the microprocessor which activates the memory facility. The microprocessor can also activate the bioprotective field coil 19 by means of a signal that passes through a digital to analogue converter 15 to a driver for the coil 17. The microprocessor also monitors the microphone of the handset to determine if the user is speaking. This information can be used to adapt the remedial signal according to the proximity of the user to the handset to optimise the protection.

Figure 4:
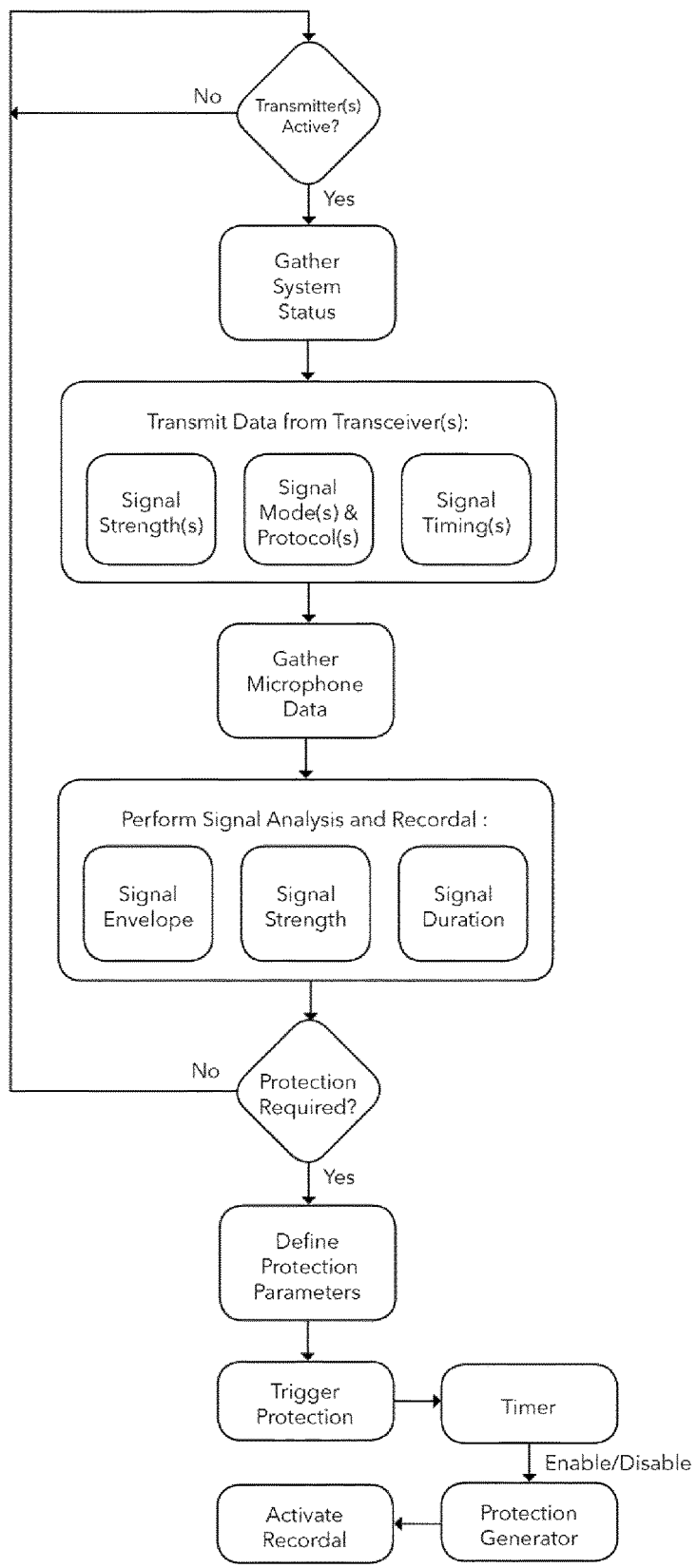

The operation of the embodiment shown in FIG. 3 is illustrated by the activity flow chart that is FIG. 4.

In the embodiment illustrated in FIG. 4 the system is initiated by the activity of the transceiver to gather information concerning the status of the system such as signal strength(s), signal mode(s) and protocol(s) and signal timing (s). Additionally information from the microphone is collected and the signals are analysed and recorded by the recordal facility, for example the signal envelope, the signal strength and the duration of the signal may be analysed and recorded. On this basis it can be determined if a protective signal is required and the nature of the protective signal and the protective signal may then be activated for an interval determined by a timer. The nature and duration of the protective signal may also be recorded.

Figure 5:
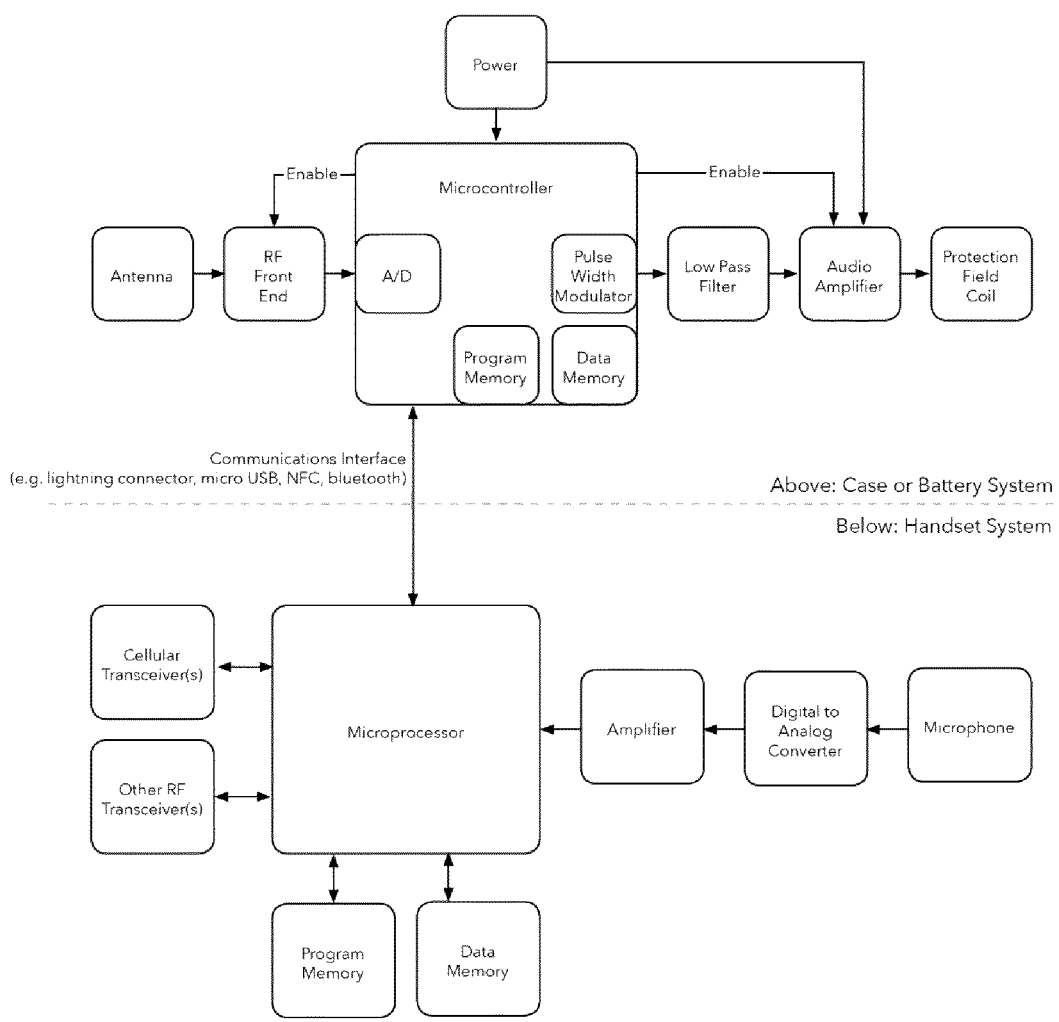

FIG. 5 illustrates the embodiment in which the case or battery is linked to the handset and shows how the link can be established.

The invention claimed is:

1. A personal communication device which detects potentially harmful radiation in radiofrequency transmissions emitted by the personal communication device, with the personal communication device comprising:
   a) a radio frequency transmitter configured to emit the radiofrequency transmissions from the personal communication device;
   b) a detector that determines when the radiofrequency transmissions are emitted by the personal communication device;
   b) a data memory facility that records one or more characteristics of the potentially harmful radiation, wherein the one or more characteristics are selected from a communication mode of the personal communication device, a protocol of the personal communication device, a modulation of the potentially harmful radiation, a strength of the potentially harmful radiation, and a duration of the potentially harmful radiation, and wherein the data memory facility is coupled with the detector;
   c) a remedial signal generator which actuates a remedial signal which is magnetic in nature and superimposed on the radiofrequency transmissions emitted by the radio frequency transmitter to reduce potential harm of the potentially harmful radiation of the radiofrequency transmissions that is detected.

2. The personal communication device according to claim 1, provided with a means for recording of the remedial signal.

3. The personal communication device according to claim 2 containing a means for transmission of data recorded concerning the remedial signal.

4. The personal communication device according to claim 3 in which the same data memory facility is employed for recording both the one or more characteristics of the potentially harmful radiation and one or more characteristics of the remedial signal.

5. The personal communication device according to claim 3 in which the means for transmission comprises a mobile telecommunication network.

6. The personal communication device according to claim 1 which further contains a means for transmission of the one or more characteristics recorded concerning the potentially harmful radiation to a remote location.

7. The personal communication device according to claim 6 in which the means for transmission comprises a mobile telecommunication network.

8. The personal communication device according to claim 1 provided with signal analysis means which can analyze the potentially harmful radiation in a way that differentiates signals that are related to voice communication and other signals including data communication.

9. The personal communication device according to claim 1, wherein the personal communication device is a battery powered telecommunication handset.

10. The personal communication device according to claim 9, wherein the detector is a utilization of one or more components within the battery powered telecommunication handset; and
   wherein at least one of the one or more components is a transceiver.

11. The personal communication device according to claim 10 in which a use of a microphone is detected in order to tailor the remedial signal.

12. The personal communication device according to claim 9, wherein the one or more characteristics of the potentially harmful radiation are recorded in the battery powered telecommunication handset.

13. The personal communication device according to claim 12, wherein the battery powered telecommunication handset includes a means for the transmission of the one or more characteristics which are recorded.

14. The personal communication device according to claim 1 in which the detector comprises an antenna coupled to a signal analysis module.

15. The personal communication device according to claim 1 in which the detector is within a battery or a case of the personal communication device.

16. The personal communication device according to claim 1 comprising an electronic circuit that comprises the detector and a microcontroller; and
   wherein the microcontroller operates the detector and the data memory facility.

17. The personal communication device according to claim 16, wherein the microcontroller operates analysis of the radiofrequency transmissions received by the detector and activates the remedial signal.

18. The personal communication device according to claim 16, wherein the detector is an RF antenna.

19. The personal communication device according to claim 1, wherein the remedial signal generator generates the remedial signal according to the one or more characteristics recorded by the data memory facility.

20. A personal communication device which detects potentially harmful radiation in radiofrequency transmissions emitted by the personal communication device, with the personal communication device comprising:
   a) a radio frequency transmitter configured to emit the radiofrequency transmissions from the personal communication device;
   b) a detector that senses a presence of the radiofrequency transmissions emitted by the personal communication device;
   c) a remedial signal generator which actuates a remedial signal which is magnetic in nature and superimposed on the radiofrequency transmissions emitted by the radio frequency to reduce potential harm of the potentially harmful radiation of the radio frequency transmissions that is detected;
   d) a data memory facility that records one or more characteristics of the potentially harmful radiation and one or more characteristics of the remedial signal;
   wherein the data memory facility is coupled with the detector;
   wherein the one or more characteristics of the potentially harmful radiation are selected from a communication mode of the personal communication device, a protocol of the personal communication device, a modulation of the potentially harmful radiation, a strength of the potentially harmful radiation, a power of the potentially harmful radiation, and a duration of the potentially harmful radiation; and
   wherein the one or more characteristics of the remedial signal are selected from a power, a strength, a frequency, and an elapsed time of the remedial signal.

21. A personal communication device which detects potentially harmful radiation in radiofrequency transmissions emitted by the personal communication device, with the personal communication device comprising:
   a) a radio frequency transmitter configured to emit the radiofrequency transmissions from the personal communication device
   b) a detector that determines when the radiofrequency transmissions are emitted by the personal communication device;
   c) a data memory facility that records one or more characteristics of the potentially harmful radiation, wherein the one or more characteristics are selected from a communication mode of the personal communication device and a protocol of the personal communication device, and wherein the data memory facility is coupled with the detector;
   d) a remedial signal generator which actuates a remedial signal which is magnetic in nature and superimposed on the radiofrequency transmissions emitted by the radio frequency transmitter to reduce potential harm of the potentially harmful radiation of the radiofrequency transmissions that is detected.

* * * * *